Figure 1:
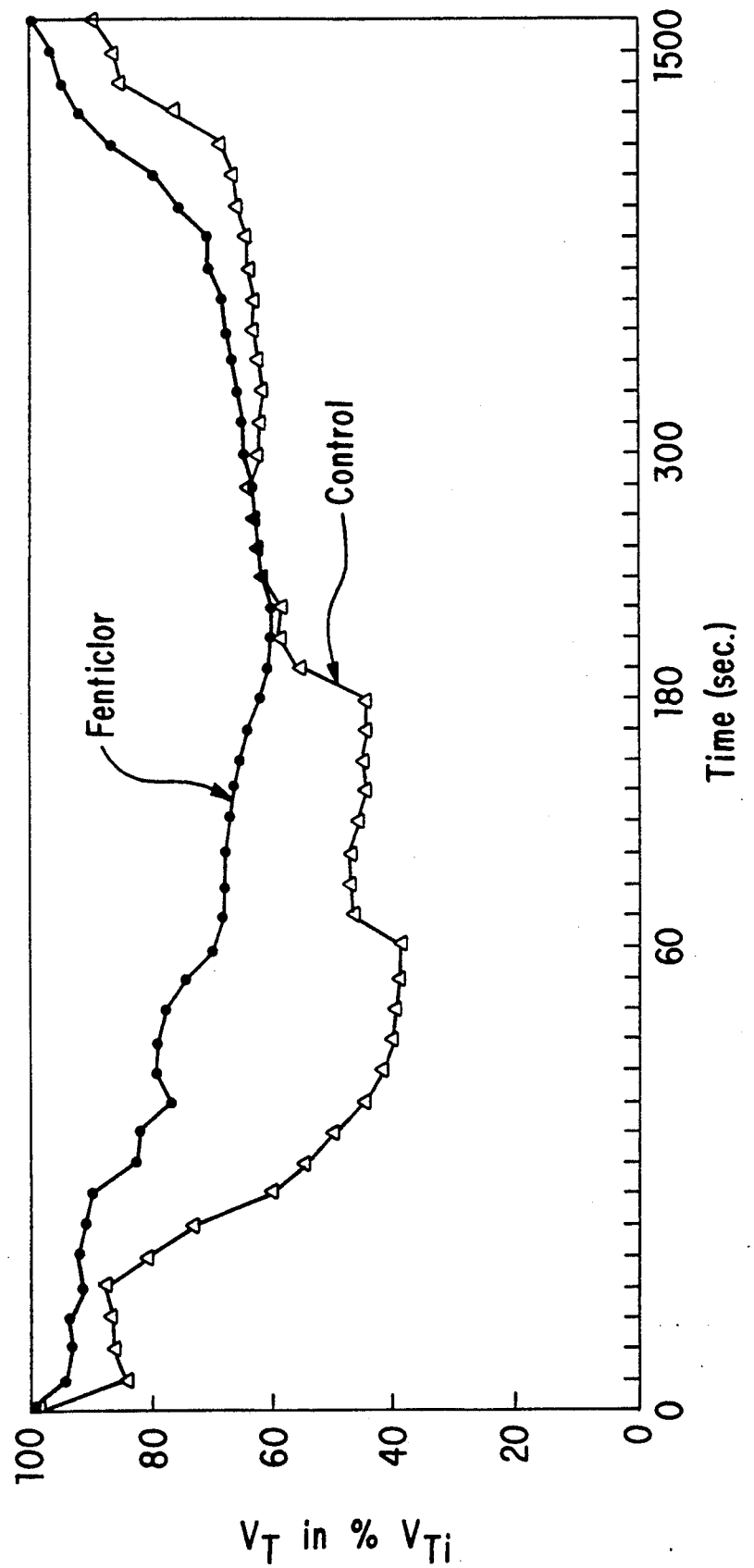

United States Patent [19]

Schewe et al.

[11] Patent Number: 5,185,377
[45] Date of Patent: Feb. 9, 1993

[54] DIPHENYL COMPOUNDS WHICH INHIBIT ARACHIDONIC ACID METABOLISM, AND THEIR USE IN PHARMACEUTICAL COMPOSITIONS

[75] Inventors: Tankred Schewe, Berlin; Helmut Luther, Freiburg; Dentscho Jordanov, Berlin, all of Fed. Rep. of Germany

[73] Assignee: Ciba-Geigy Corporation, Ardsley, N.Y.

[21] Appl. No.: 754,788

[22] Filed: Sep. 4, 1991

[30] Foreign Application Priority Data

Sep. 5, 1990 [CH] Switzerland ............... 2875/90

[51] Int. Cl.$^5$ ............................................. A61K 31/075
[52] U.S. Cl. ................................. 514/721; 514/712; 514/735; 514/826; 514/863; 514/946
[58] Field of Search .................. 514/721, 712, 735

[56] References Cited

U.S. PATENT DOCUMENTS

| | | | |
|---|---|---|---|
| 4,512,987 | 4/1985 | Schindlery | 514/171 |
| 4,735,802 | 4/1988 | La | 424/154 |
| 4,942,029 | 7/1990 | Scheps | 424/78 |

FOREIGN PATENT DOCUMENTS

| | | |
|---|---|---|
| 0220890 | 5/1987 | European Pat. Off. |
| 0271332 | 6/1988 | European Pat. Off. |
| 2148116A | 5/1985 | United Kingdom |
| 2207605A | 2/1989 | United Kingdom |

OTHER PUBLICATIONS

Chemical Abstracts 78:110767y (1973).
Chemical Abstracts 82:7629p (1975).
Clinical Trials Journal 24 (3) 1987, pp. 222–226.
Contact Dermatitis 18 (4) 1988, pp. 243–244.
J. Periodont. Res. 24 (1) 1989, pp. 75–80.
Biomed. Biochim. Acta 42, 1309 (1983).
European J. Pharmacol. 86, 207 (1983).
Z. Erkrank, Atm-org. 171, 85 (1988).
Prostaglandins and Related Substances, p. 229, IRL Press, Oxford, Washington (1987).
Respiration 50, Supplement 2, 22 (1986).
Photodermatol 359, 66 (1985).
Ring, J.; New Trends in Allergy II, p. 78, Springer Verlag, Heidelberg (1985).
J. Pharma. Pharmacol. 17, 384 (1965).
J. Appl. Physiol 58, 834 (1985).
Z. Erkrank Atm.-org. 166, 223 (1986).
Eur. J. Biochem, 96, 545 (1979).
J. Int. Med. Res. 15, 383 (1987).
Brit. J. Pharmacol. 77, 301 (1982).
Methods Enzymol. 86, 60 (1982).
Piper, P. J.: The Leukotrienes: Their Biological Significance, p. 175, Raven Press, N.Y. 1986.
Clin. Rev. Allergy 1, 369 (1983).
Arch. Pharmacol. 338, 417 (1988).

Primary Examiner—Leonard Schenkman
Attorney, Agent, or Firm—Edward McC. Roberts

[57] ABSTRACT

Pharmaceutical compositions, which comprise a compound of the general formula I

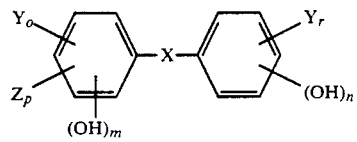

in which X is oxygen, sulfur or $-CH_2-$, Y is chlorine or bromine, Z is an $SO_2H$, $NO_2$ or $C_1-C_4$alkyl radical, r is a number from 0 to 3, o is a number from 0 to 3, p is the number 0 or 1, m is the number 1 or 2 and n is the number 0 or 1, have having a lipoxygenase- and prostaglandin H synthase-inhibiting action.

The compositions are useful in particular for the local (topical) or inhalative treatment of inflammatory, allergic and spasmolytic diseases, as well as psoriasis, bronchial asthma and diseases with disturbances in cell proliferation.

7 Claims, 2 Drawing Sheets

DIPHENYL COMPOUNDS WHICH INHIBIT ARACHIDONIC ACID METABOLISM, AND THEIR USE IN PHARMACEUTICAL COMPOSITIONS

The invention relates to pharmaceutical compositions containing liopxygenase- and prostaglandin H synthase-inhibiting active ingredients for preferably topical application in human and veterinary medicine. They are used in particular for the treatment of inflammatory skin diseases of non-microbial origin, for example psoriasis, skin erythemas, fibroproliferative diseases and allergic diseases, and bronchial asthma.

Glucocorticoids are preferably used for the topical treatment of inflammatory and allergic diseases. It is generally known that these substances have undesirable side effects.

Non-steroidal anti-inflammatory medicaments which contain active ingredients such as ketoprofen, BW 755 c, pyroxicam, diclofenac or indomethacin cannot be used effectively on a limited local area but only systemically because of their inadequate skin penetration (cf., for example, G. B. Kasting et al., Pharmacol. Sci., Volume 1, pp. 138–153, Karger, Basel 1987). 2-Hydroxy-diphenyl ethers, 2-hydroxy-diphenylmethanes and 2-hydroxy-diphenyl thioethers which have a good skin penetration have hitherto been claimed (DRP 568 944, CH 428 758, DE 1 216 882) or used [for example H. Abdel Aal et al., J. Int. Med. Res. 15, 383 (1987)] as constituents of pharmaceutical preparations only for an antimicrobial activity.

The treatment of inflammatory diseases based on a disturbance in endogenous regulation of metabolism using the compounds mentioned is unknown.

The aim of the invention is to provide pharmaceutical compositions having pharmacologically useful properties, in particular anti-inflammatory, anti-psoriatic, cell proliferation-regulating, antiallergic, spasmolytic, gastroprotective and antiasthmatic properties, when used, in particular, locally and/or by inhalation.

The object of the invention is to develop pharmaceutical compositions which have anti-inflammatory, antiallergic and other pharmacologically useful properties which are based, in particular, or inhibition of the oxygenation reactions of arachidonic acid metabolism, and show no undesirable side effects when used locally.

Surprisingly, it has been found that, according to the invention, 2-hydroxy-diphenyl ethers, 2-hydroxy-diphenylmethanes and 2-hydroxy-diphenyl thioethers, which are known per se, of the general formula I

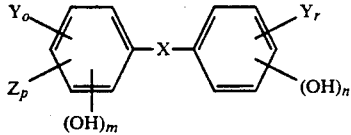

in which X is oxygen, sulfur or —CH$_2$—, Y is chlorine or bromine, Z is SO$_2$H, NO$_2$ or C$_1$-C$_4$alkyl, r=0 to 3, o=0 to 3, p=0 or 1, m=1 or 2 and n=0 or 1, showed pronounced actions.

The anti-inflammatory, antiallergic and antiasthmatic activity is demonstrated in cellular in vitro studies and in studies in vitro and in vivo in animal experiments.

Preferred are compounds of the formula I

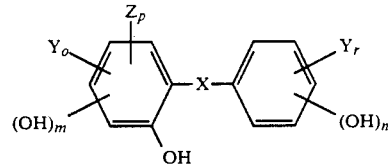

in which X is oxygen, sulfur or —CH$_2$—, Y is chlorine or bromine, Z is SO$_2$H, NO$_2$ or C$_1$-C$_4$alkyl, r=0 to 3, o=0 to 3, p=0 or 1, m=0 or 1 and n=0 or 1.

Compounds of the formula (I) in which X is oxygen, sulfur or —CH$_2$—, Y is chlorine or bromine, m=0, n=0 or 1, o=1 or 2, r=1 or 2 and p=0 are of particular interest.

Compounds of the formula (I) in which X is oxygen, Y is chlorine, m=0, o=1, r=2 and p=0 are of very particular interest.

The compounds of the general formula (I) cause a dose-related reduction in arachidonic acid-induced contraction of isolated lung parenchyma strips and isolated tracheal spirals of the guinea-pig (Example 1). These are in both cases proven in vitro models for antiasthmatic actions based on an influence on the arachidonic acid metabolism in lung tissue [J. Slapke et al., Biomed. Biochim. Acta 42, 1309 (1983); and S.-E. Dahlén et al., Eur. J. Pharmacol. 86, 207 (1983)].

The specific allergic bronchoconstriction in ovalbumin-sensitised, anaesthetised and artificially respirated guinea-pigs [according to P. Andersson, Brit. J. Pharmacol. 77, 301 (1982)] is further more considerably reduced by the compounds I mentioned (Example 2).

In the in vivo asthma model of intratracheal instillation of arachidonic acid in the guinea-pig [according to G. Becher et al., Z. Erkrank. Atm.-org. 171, 85 (1988)], the bronchoconstriction is significantly reduced by the compounds mentioned (Example 3).

Low concentrations of the compounds I furthermore inhibit purified erythroid 15-lipoxygenase of rabbits [according to Schewe, T.; Kühn, H.; Rapoport, S. M.; in: Benedetto, C.; McDonald-Gibson, R. C.; Nigam, S.; Slater, T. F. (editors): Prostaglandins and related substances, pages 229, IRL Press, Oxford, Washington 1987] (Example 4) and prostaglandin H synthase from sheep seminal vesicles [according to Van der Ouderaa, F. J. G. et al., Methods Enzymol. 86, 60 (1982) (Example 5).

Eicosanoids, which are formed by lipoxygenases or prostanglandin H synthase from arachidonic acid in mammalian cells, play a key role in the pathogenesis of bronchial asthma [Dahlén, S.-R. et al., Respiration 50, Supplement 2, 22 (1986)], psoriasis [Greaves, M. W.; in Piper, P. J. (editor): The Leukotrienes: Their Biological Significance, pages 175, Raven Press, New York, 1986], dermatitis induced by UV light [Sondergaard, J. et al., Photodermatol. 359, 66 (1985)] and a wide range of allergic syndromes [Stetson, W. F. et al. Clin. Rev. Allergy 1, 369 (1983); Parker, C. W. in: Ring, J. (editor): New Trends in Allergy II, pages 137, Springer-Verlag, Heidelberg 1985]. The compounds I accordingly have a curative action according to the invention, directly or as a constituent of pharmaceutical preparations together with one or more pharmaceutically acceptable carriers, for all forms of bronchial asthma, allergic diseases, fibroproliferative diseases, psoriasis, skin erythemas and other inflammatory diseases of non-microbial origin.

Pharmaceutical forms which comprise the compounds of the formula I are to be understood as meaning, in particular forms that are useful for local (topical) or inhalatory treatment as emulsions, ointments, gels, sprays, powders and the like. Compounds of the formula I can also be contained in liposomes or be used in pharmacological preparations together with customary carriers and/or penetration accelerators, for example urea, propylene glycol, oleic acid and the like [cf. also Barry, B. W. in: Schroot, B.; Schaefer, H. (editors): Pharmacol. Skin., Volume 1, pages 121, Karger, Basle 1987). Compounds of the formula I and those in pharmaceutical preparations according to the invention are in general present in amounts of 0.01 to 15, preferably 0.1 to 4, % by weight of the total mixture. For treatment of the diseases mentioned, the pharmaceutical preparations according to the invention can also comprise other pharmaceutical active ingredients in addition to the compounds of the formula I, for example anti-inflammatory, antipsoriatic, cell proliferation-regulating, antiallergic spasmolytic, gastroprotective and antiasthmatic active ingredients.

EXAMPLE 1

Action of 2,4,4'-trichloro-2'-hydroxy-diphenyl ether (triclosan) and 2,2'-dihydroxy-5,5'-dichloro-diphenyl sulfide (fenticlor) or arachidonic acid-induced contraction of isolated tracheal and lung parenchyma preparations Testing of antiasthmatic active qualities of triclosan and fenticlor in vitro is carried out on isolated tracheal spirals and lung parenchyma strips of adult guinea-pigs (250-500 g) of both sexes. The tracheal spirals are prepared by the method described by Constantine [J. W. Constantine et al., J. Pharm. Pharmacol. 17, 384 (1965)]. Particular emphasis is placed on complete removal of the surrounding connective tissue and on maintaining the integrity of the epithelium [N. A. Flavahan et al., J. Appl. Physiol. 58, 834 (1985)].

The lung parenchyma strip is prepared in accordance with the method described by Del Monte [L. Del Monte et a., Naunym-Schmiedebergs Arch. Pharmacol., 338, 417 (1988)]. The contraction of the isolated organs is determined as isotonic measurement of the path under standardised conditions [J. Slapke et al., Biomed. Biochim. Acta 42, 1309 (1983)] in a multiple organ bath.

A modified Krebs-Henseleit solution (pH=7.4) of the following composition is used for the studies (m×mol $1^{-1}$): NaCl 134.8, KCl 5.9, Tris 10.02, $CaCl_2$ 1.82, $MgCl_2$ 1.145, glucose 1.11. Air is used for gassing. The bath temperature is 37° C. for the lung parenchyma strips and 35° C. for the tracheal spirals. Conditioning of the preparations is performed several times with $5 \times 10^{-4}$ M acetylcholine to obtain the standardisation value, this substance subsequently being flushed out. In all studies, the contractions are induced by addition of arachidonic acid to the organ bath in increasing concentrations and are measured cumulatively. All the measurements are made in the present of 5 μM indomethacin.

Arachidonic acid causes a concentration-related contraction on the two preparations, with an average $ED_{50}$ value of $10^{-4}$ M for lung strips and $5 \times 10^{-5}$ M for tracheal spirals.

Triclosan

Triclosan in a concentration of $10^{-6}$ M leads to complete inhibition of the arachidonic acid-induced contraction ($10^{-7}$–$10^3$ M) on isolated lung parenchyma strips.

In contrast, ketotifen in a concentration of $10^{-6}$ M causes only a 25% inhibition on the same preparation, and $5 \times 10^{-5}$ M nordihydroguarjiaretic acid and $5 \times 10^{-5}$ M BW 755 C causes in each case only 50% inhibition.

Under the same test conditions, triclosan in concentrations of $>10^{-6}$ M induces a pronounced dose-related relaxation on isolated lung parenchyma strips. In the presence of $5 \times 10^{-6}$ M or $5 \times 10^{-5}$ M triclosan, the arachidonic acid concentration which causes relaxation of half the maximum is $ID_{50} = 3 \times 10^{-6}$ M.

The corresponding value on the tracheal spirals is $ID_{50} = 10^{-6}$ M.

Fenticlor

Isolated lung parenchyma strips:

$ID_{50} = 5 \times 10^{-6}$ M

Isolated tracheal spirals:

Isolated tracheal spirals:

$IE_{50}32\ 1 \times 10^{-5}$ M

EXAMPLE 2

Effect of fenticlor on ovalbumin-induced bronchoconstriction in the ovalbumin-sensitised guinea-pig Guinea-pigs are sensitised i.p. with 10 μg of ovalbumin and 100 mg of aluminium hydroxide in 0.5 ml of isotonic saline solution by the method of Anderson [P. Anderson, Brit. J. Pharmacol. 77, 301 (1982)]. After 14 days, the conscious animals are given a booster by inhalation of a 0.1% strength atomised ovalbumin solution. Only animals with a positive reaction are used for comparison from the fourth day after the booster. Guinea-pigs with a body weight of 450-550 g are were anaesthetised with 1.3 g/kg of ethylurethane i.p. Thereafter, a cannula is connected to the trachea. The animals are relaxed with 0.2 mg/kg pancuronium bromide i.v. and respirated in a tank respirator (f=20/min, p.=3 pPa, I:E=1:1). The animals breath in air from the room by the tracheal cannula led to the outside. The tidal volume $V_T$ is measured pneumota- chographically. 1 mg/kg of ovalbumin in 300 μl of water is instilled intratracheally to induce the spasm [G. Becher et al., Z. Erkrankg., Arm.-org. 166, 223 (1986)].

FIG. 1 shows the course of the tidal volume with respect to time during unchanged artificial respiration in percent of the starting value for the control animals (n=6) and for experimental animals (n=6) pretreated with 100 mg/kg of fenticlor p.o. 2 hours before the experiment.

The allergic reaction is reduced significantly by pretreatment with fenticlor in comparison with the controls. The maximum bronchospasm is inhibited to the extent of 60%, and a return to the starting volume is achieved after 25 minutes.

Statistical analysis of the results is carried out with the parameter-free U-test according to Mann and Whitney, $p. \leq 0.05$.

EXAMPLE 3

Effect of fenticlor on arachidonic acid-induced bronchoconstruction in the guinea-pig A bronchospasm is induced in non-sensitised guinea-pigs in the same experimental design as in Example 2 by intratracheal instillation of 2 mg/kg of Na arachidonate solution in phosphate buffer pH=7.4 [G. Becher et al., Z. Erkrankg. Atm.-org. 171, 85 (1988)].

Figure 2:
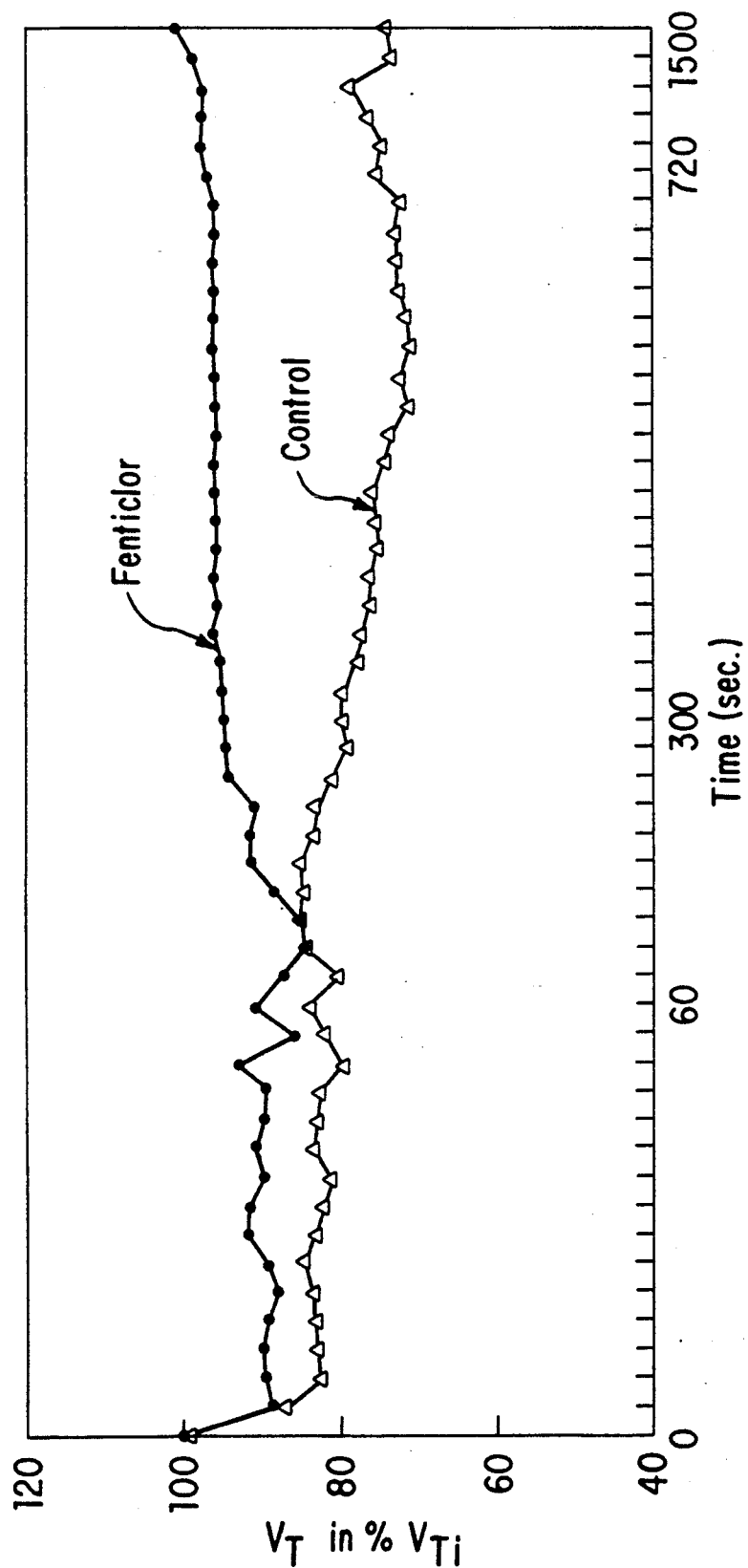

FIG. 2 shows the course of the tidal volume with respect to time during unchanged artificial respiration in percent of the starting value for the control animals (n=6) and for experimental animals (n=6) pretreated with 100 mg/kg of fenticlor p.o. 2 hours before the experiment.

The arachidonic acid-induced bronchoconstrictive reaction is inhibited significantly (parameter-free U-test according to Mann and Whitney, $p \leq 0.05$) from the fifth minute by pretreatment with fenticlor. The maximum bronchospasm is inhibited to the extent of 16.5%, and a return to the starting volume is achieved after 25 minutes.

EXAMPLE 4

Inhibition of the activity of 15-lipoxygenase from rabbit reticulocytes

The lipoxygenase from rabbit reticulocytes is obtained in an electrophoretically and immunologically pure form by the method described in the literature [S. M. Rapoport et al., Eur. J. Biochem. 96, 545 (1979)]. The lipoxygenase activity is determined at 25° C. via amperometric measurement of the $O_2$ consumption by means of a Clark electrode in the following system: 0.1 M potassium phosphate pH 7.4 containing 0.2% of sodium cholate and 0.53 mM linoleic acid. The enzyme concentration in the measurement bath is 25 nM. The substances to be tested are added as a solution in methylglycol (freshly distilled). The dilutions of the compounds are chosen so that the final concentrations of methylglycol in the preincubation series does not exceed 2%; no noticeable inhibitions occurres in the control batches under these conditions. The enzyme reaction is started by addition of sodium cholate and linoleic acid. The titration curve of the inhibition and from this the concentration needed for 50% inhibition are determined by varying the active ingredient concentration.

The results are shown in Table 1

TABLE 1

|  | 15-LOX $IC_{50}$ ($\mu M$) |
| --- | --- |
| 2,4,4'-Trichloro-2'-hydroxy-diphenyl ether (triclosan) | 2.4 |
| 2,2'-Dihydroxy-5,5'-dichloro-diphenyl sulfide (fenticlor) | 1.4 |
| 2,2'-Dihydroxy-3,3',5,5'-tetrachloro-diphenylmethane | 9.5 |
| 2,2'-Dihydroxy-3,3',5,5'-tetrabromo-diphenylmethane | 2.8 |
| 2,2'-Dihydroxy-3,3'-dichloro-5,5'-dibromo-diphenylmethane | 3.8 |
| 4,4'-Dihydroxy-3,3',5,5'-tetrabromo-diphenylmethane | 5.0 |
| 4,4'-Dihydroxy-3,3'-dibromo-5,5'-dichloro-diphenylmethane | 10.5 |
| 2,2'6,6'-Tetrahydroxy-3,3',5,5'-tetrachloro-diphenylmethane | 3.6 |
| 2,2'-Dihydroxy-3,3',5,5',6,6'-hexachloro-diphenylmethane | 3.5 |
| 2-Benzyl-4-chlorophenol (chlorophene) | 2.0 |
| 4-Chloro-2-methyl-6-benzylphenol | 2.5 |
| 2-Chloro-6-methyl-4-benzylphenol | 28.0 |

EXAMPLE 5

Inhibition of the activity of prostaglandin H synthase from sheep seminal vesicles Prostaglanding H synthase from sheep seminal vesicles is obtained by the method described in the literature by Van der Oudaraa, F. J. G.; Buytenhek, M.; Methods Enzymol. 86, 60 (1982).

The enzyme activity is determined at 25° C. by polargraphic measurement of the oxygen consumption with a Clark electrode.

The measurement batch consists of 400 $\mu m$ $ml^{-1}$ of prostaglandin H synthase in 0.1 M Tris-HCl buffer pH=8.0, 5 mM tryptophan, 1 $\mu M$ haemin and 0.124 mM arachidonic acid. The substances to be tested are dissolved in methylglycol and incubated with the enzyme in the absence of arachidonic acid for 10 minutes at 25° C. The enzyme reaction is started with arachidonic acid.

The titration curve of the inhibition and from this the concentration needed for 50% inhibition are determined by varying the active ingredient concentration.

The results are shown in Table 2

TABLE 2

|  | PG H synthase $IC_{50}$ ($\mu M$) |
| --- | --- |
| 2,4,4'-Trichloro-2'-hydroxy-diphenyl ether (triclosan) | 23.0 |
| 2,2'-Dihydroxy-5,5'-dichloro-diphenyl sulfide (fenticlor) | 15.5 |
| 2,2'-Dihydroxy-3,3',5,5'-tetrachloro-diphenylmethane | 60.0 |
| 2,2'-Dihydroxy-3,3',5,5'-tetrabromo-diphenylmethane | 45.0 |
| 2,2'-Dihydroxy-3,3'-dichloro-5,5'-dibromo-diphenylmethane | 28.0 |
| 4,4'-Dihydroxy-3,3',5,5'-tetrabromo-diphenylmethane | 17.0 |
| 4,4'-Dihydroxy-3,3'-dibromo-5,5'-dichloro-diphenylmethane | 180.0 |
| 2,2',6,6'-Tetrahydroxy-3,3',5,5'-tetrachlorodiphenylmethane | 17.0 |
| 2,2'-Dihydroxy-3,3',5,5',6,6'-hexachloro-diphenylmethane | 17.0 |
| 2-Benzyl-4-chlorophenol (chlorophene) | 40.0 |
| 4-Chloro-2-methyl-6-benzylphenol | 30.0 |
| 2-Chloro-6-methyl-4-benzylphenol | 35.0 |

The following examples illustrate the invention described above without limiting it. Temperatures are given in degrees Celsius.

PREPARATION EXAMPLE 1

An ointment comprising 0.05% of 2,4,4'-trichloro-2'-hydroxy-diphenyl ether can be prepared as follows:

| Composition | |
| --- | --- |
| Active ingredient | 0.05% |
| Vaseline | 45.0% |
| Liquid paraffin | 19.6% |
| Cetyl alcohol | 5.00% |
| Beeswax | 5.00% |
| Sorbitan sesquioleate | 5.00% |
| p-Hydroxybenzoate | 0.20% |
| Water, demineralised, up to | 100.00% |

The fats and emulsifiers are melted together and the active ingredient is dissolved therein.

The preservative is dissolved in water, the solution is emulsified into the fatty melt at elevated temperature and the emulsion is stirred until cold.

PREPARATION EXAMPLE 2

A cream comprising 0.5% of 2,4,4'-trichloro-2'-hydroxy-diphenyl ether can be prepared as follows:

| Composition: | |
|---|---|
| Active ingredient | 0.5% |
| Isopropyl palmitate | 8.0% |
| Cetyl palmitate | 1.5% |
| Silicone oil 100 | 0.5% |
| Sorbitan monostearate | 3.0% |
| Polysorbate 60 | 3.5% |
| 1,2-Propylene glycol PH | 20.0% |
| Acrylic acid polymer | 0.5% |
| Triethanolamine | 0.7% |
| Water, demineralised, up to | 100.00% |

The acrylic acid polymer is suspended in a mixture of demineralised water and 1,2-propylene glycol. Triethanolamine is then added, while stirring, a mucilage being obtained. A mixture of isopropyl palmitate, cetyl palmitate, silicone oil, sorbitan monostearate and polysorbate is heated to about 75° and the active ingredient is dissolved therein. This fatty phase is incorporated, while stirring, into the mucilage, which is likewise heated to about 75°, and the mixture is stirred until cold.

PREPARATION EXAMPLE 3

A cream comprising 0.05% of 2,4,4'-trichloro-2'-hydroxy-diphenyl ether can be prepared as follows:

| Composition: | |
|---|---|
| Active ingredient | 0.05% |
| Cetyl palmitate PH | 2.00% |
| Cetyl alcohol PH | 2.00% |
| Triglyceride mixture of saturated medium-chain fatty acids | 5.00% |
| Stearic acid | 3.00% |
| Glycerol stearate PH | 4.00$ |
| Cetomacrogol 1000 | 1.00% |
| Microcrystalline cellulose | 0.50% |
| 1,2-Propylene glycol, distilled | 20.00% |
| Water, demineralized, up to | 100.00% |

The cetyl alcohol, cetyl palmitate, triglyceride mixture, stearic acid and glycerol stearate are melted together and the active ingredient is dissolved therein. The microcrystalline cellulose is dissolved in some of the water. The cetomacrogol is dissolved in the remainder of the water, and the propylene glycol and mucilage are mixed with this solution. The fatty phase is then added to the aqueous phase, while stirring, and the mixture is stirred until cold.

PREPARATION EXAMPLE 4

A transparent hydrogel comprising 0.5% of 2,4,4'-trichloro-2'-hydroxy-diphenyl ether is prepared as follows:

| Composition: | |
|---|---|
| Active ingredient | 0.5% |
| Propylene glycol | 10.0–20.0% |
| Isopropanol | 20.0% |
| Hydroxypropyl-methylcellulose | 2.0% |
| Water | to 100.00% |

The hydroxypropyl-methycellulose is swollen in water. The active ingredient is dissolved in a mixture of the isopropanol and propylene glycol. The active ingredient solution is then mixed with the swollen cellulose derivative and, if desired, odiferous substances (0.1%) are added.

PREPARATION EXAMPLE 5

A transparent hydrogel comprising 0.005% of 2,4,4'-trichloro-2'-hydroxy-diphenyl ether is prepared as follows:

| Composition: | |
|---|---|
| Active ingredient | 0.005% |
| Propylene glycol | 20.0% |
| Isopropanol | 20.0% |
| Acrylic acid polymer | 2.0% |
| Triethanolamine | 3.0% |
| Water | to 100.00% |

The acrylic acid polymer and water are dispersed and the dispersion is neutralised with the triethanolamine. The active ingredient is dissolved in a mixture of isopropanol and propylene glycol. The active ingredient solution is then mixed with a gel, it being possible to add an odiferous substance (0.1%) if desired.

PREPARATION EXAMPLE 6

A foam spray comprising 0.01% of 2,4,4'-trichloro-2'-hydroxy-diphenyl ether can be prepared as follows:

| Composition: | |
|---|---|
| Active ingredient | 0.01% |
| Cetyl alcohol PH | 1.70% |
| Liquid paraffin, heavy | 1.00% |
| Isopropyl myristate | 2.00% |
| Cetomacrogol 1000 | 2.40% |
| Sorbitan monostearate | 1.50% |
| 1,2-Propylene glycol PH | 5.00% |
| Methylparaben | 0.18% |
| Propylparaben | 0.02% |
| Chemoderm 314 | 0.10% |
| Water, demineralised, up to | 100.00% |

The cetyl alcohol, liquid paraffin, isopropyl myristate, cetomacrogol and sorbitan stearate are melted together and the active ingredient is dissolved therein. The methyl- and propylparaben are dissolved in the propylene glycol and added to the hot water. The melt and the solution are then mixed. After cooling, the Chemoderm is added and the mixture is made up to the final weight with water.

Packaging:

20 ml of the mixture are introduced into an aluminium can. The can is provided with a valve and the propellent gas is introduced under pressure.

PREPARATION EXAMPLE 7

An eye ointment comprising 1% of 2,4,4'-trichloro-2'-hydroxy-diphenyl ether can be prepared as follows:

| Composition: | |
|---|---|
| Active ingredient | 1% |
| Liquid paraffin, heavy | 10% |
| Wool fat, anhydrous | 10% |
| Vaseline, white | 79% |
| | 100% |

The constituents are melted together and the mixture is subjected to sterile filtration.

PREPARATION EXAMPLE 8

Capsules comprising 0.025 g of 2,4,4'-trichloro-2'-hydroxy-diphenyl ether which are suitable for insufflation can be prepared as follows:

| Composition: (for 1000 capsules) | |
| --- | --- |
| Active ingredient | 25.00 g |
| Lactose, ground | 25.00 g |

The active ingredient and the very finely ground lactose are mixed thoroughly with one another. The resulting powder is sieved and gelatin capsules are filled with portions of in each case 0.05 g.

What is claimed is:

1. A method for the local and/or inhalative treatment of inflammation, allergy, bronchoconstriction, bronchial asthma or diseases with disturbances in cell proliferation in mammals, which comprises applying to a mammal in need thereof a pharmaceutical composition consisting essentially of 0.01 to 15% by weight of a compound of the formula

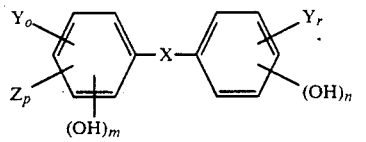

in which X is oxygen, sulfur of —$CH_2$—, Y is chlorine or bromine, Z is $SO_2H$, $NO_2$ or $C_1$–$C_4$alkyl, r is a number from 0 to 3, o is a number from 0 to 3, p is one of the numbers 0 or 1, m is one of the numbers 1 or 2 and n is one of the numbers 0 or 1, and a carrier.

2. A method of claim 1 wherein the disease with disturbances in cell proliferation is psoriasis.

3. A method of claim 1, wherein an OH-group of $(OH)_m$ is ortho to the bridge X.

4. A method of claim 3, wherein m is 1, o is 1 or 2, r is 1 or 2, and p is 0.

5. A method of claim 3, wherein X is oxygen, Y is chlorine, m is 1, n is 0, o is 1, r is 2, and p is 0.

6. A method of claim 1, wherein the composition additionally comprises a penetration accelerator.

7. A method of claim 6, wherein the penetration accelerator is selected from the group comprising of urea, propylene glycol and oleic acid.

* * * * *